(12) United States Patent
Hojeibane et al.

(10) Patent No.: US 7,128,718 B2
(45) Date of Patent: Oct. 31, 2006

(54) GUIDEWIRE WITH DEFLECTABLE TIP

(75) Inventors: Hikmat Hojeibane, Princeton, NJ (US); David Grewe, Glen Gardner, NJ (US)

(73) Assignee: Cordis Corporation, Miami Lakes, FL (US)

( * ) Notice: Subject to any disclaimer, the term of this patent is extended or adjusted under 35 U.S.C. 154(b) by 659 days.

(21) Appl. No.: 10/224,168

(22) Filed: Aug. 20, 2002

(65) Prior Publication Data

US 2003/0181827 A1 Sep. 25, 2003

Related U.S. Application Data

(60) Provisional application No. 60/366,739, filed on Mar. 22, 2002.

(51) Int. Cl.
*A61B 5/00* (2006.01)
*A61M 25/00* (2006.01)

(52) U.S. Cl. ..................................................... 600/585

(58) Field of Classification Search ............... 600/433, 600/434, 435, 585; 604/164.01, 164.13, 604/170.01
See application file for complete search history.

(56) References Cited

U.S. PATENT DOCUMENTS

| | | | |
|---|---|---|---|
| 4,003,369 A | 1/1977 | Heilman et al. | |
| 4,665,906 A | 5/1987 | Jervis | |
| 4,719,924 A | 1/1988 | Crittenden et al. | |
| 4,757,827 A * | 7/1988 | Buchbinder et al. | 600/585 |
| 4,770,188 A | 9/1988 | Chikama | |
| 4,813,434 A | 3/1989 | Buchbinder et al. | |
| 4,815,478 A | 3/1989 | Buchbinder et al. | |
| 4,827,941 A | 5/1989 | Taylor et al. | |
| 4,854,325 A | 8/1989 | Stevens | |
| 4,875,489 A | 10/1989 | Messner et al. | |
| 4,881,981 A | 11/1989 | Thoma et al. | |
| 4,886,067 A | 12/1989 | Palermo | |
| 4,921,482 A | 5/1990 | Hammerslag et al. | |
| 4,923,462 A | 5/1990 | Stevens | |
| 4,925,445 A | 5/1990 | Sakamoto et al. | |
| 4,935,088 A | 6/1990 | Mitsuyama | |
| 4,936,845 A | 6/1990 | Stevens | |
| 4,940,062 A | 7/1990 | Hampton et al. | |
| 4,953,553 A | 9/1990 | Tremulis | |
| 4,966,163 A | 10/1990 | Kraus et al. | |
| 4,984,581 A | 1/1991 | Stice | |
| 4,998,916 A | 3/1991 | Hammerslag et al. | |
| 5,037,391 A | 8/1991 | Hammerslag et al. | |

(Continued)

FOREIGN PATENT DOCUMENTS

EP  0274412 B1  7/1988

(Continued)

OTHER PUBLICATIONS

European Search Report dated Oct. 29, 2003, for European Patent Application No. 03251773.2.

(Continued)

*Primary Examiner*—Max F. Nindenburg
*Assistant Examiner*—Jonathan Foreman
(74) *Attorney, Agent, or Firm*—Henry W. Collins (57) ABSTRACT

A bi-directional steerable guidewire having a deflectable distal tip which comprises a longitudinal hypotube and a spring coil attached to the distal end of the hypotube and also includes a longitudinally movable deflection member which is attached to the distal end of the spring coil and a tip retaining member which extends from the distal end of the hypotube to the distal end of the spring coil for providing very precise deflection of the distal tip.

29 Claims, 6 Drawing Sheets

U.S. PATENT DOCUMENTS

| | | |
|---|---|---|
| 5,060,660 A | 10/1991 | Gambale et al. |
| 5,069,226 A | 12/1991 | Yamauchi et al. |
| 5,078,722 A | 1/1992 | Stevens |
| 5,116,350 A | 5/1992 | Stevens |
| 5,120,308 A | 6/1992 | Hess |
| 5,125,395 A | 6/1992 | Adair |
| 5,133,364 A | 7/1992 | Palermo et al. |
| 5,143,085 A | 9/1992 | Wilson |
| 5,159,937 A | 11/1992 | Tremulis |
| 5,188,621 A | 2/1993 | Samson |
| 5,190,050 A | 3/1993 | Nitzsche |
| 5,203,772 A | 4/1993 | Hammerslag et al. |
| 5,242,394 A | 9/1993 | Tremulis |
| 5,341,818 A | 8/1994 | Abrams et al. |
| 5,365,942 A * | 11/1994 | Shank .......... 600/585 |
| 5,368,049 A | 11/1994 | Raman et al. |
| 5,372,587 A | 12/1994 | Hammerslag et al. |
| 5,397,305 A | 3/1995 | Kawula et al. |
| 5,480,382 A | 1/1996 | Hammerslag et al. |
| 5,501,694 A | 3/1996 | Ressemann et al. |
| 5,695,111 A | 12/1997 | Nanis et al. |
| 5,807,279 A | 9/1998 | Viera |
| 5,813,997 A | 9/1998 | Imran et al. |
| 5,882,333 A | 3/1999 | Schaer et al. |
| 5,891,055 A | 4/1999 | Sauter |
| 5,908,405 A | 6/1999 | Imran et al. |
| 5,931,830 A | 8/1999 | Jacobsen et al. |
| 6,027,460 A | 2/2000 | Shturman |
| 6,059,739 A | 5/2000 | Baumann |
| 6,126,649 A | 10/2000 | VanTassel et al. |
| 6,146,338 A | 11/2000 | Gardeski et al. |
| 6,193,706 B1 | 2/2001 | Thorud et al. |
| 6,273,876 B1 | 8/2001 | Klima et al. |
| 6,306,105 B1 | 10/2001 | Rooney et al. |
| 6,352,515 B1 | 3/2002 | Anderson et al. |
| 6,355,016 B1 | 3/2002 | Bagaoisan et al. |
| 6,375,628 B1 | 4/2002 | Zadno-Azizi et al. |
| 6,379,369 B1 | 4/2002 | Abrams et al. |
| 6,468,230 B1 | 10/2002 | Muni et al. |
| 6,488,637 B1 | 12/2002 | Eder et al. |
| 2002/0019599 A1 | 2/2002 | Rooney et al. |
| 2002/0049392 A1 | 4/2002 | DeMello |
| 2002/0151966 A1 | 10/2002 | Eder et al. |
| 2002/0165534 A1 | 11/2002 | Hayzelden et al. |

FOREIGN PATENT DOCUMENTS

| | | |
|---|---|---|
| EP | 0 377 269 B1 | 2/1993 |
| WO | WO 03/051446 A1 | 6/2003 |

OTHER PUBLICATIONS

European Search Report dated Sep. 2, 2006 for European Patent Application No. 04266553.1.

And European Search Report dated Jan. 6, 2006 for European Patent Application No. 04254537.4.

* cited by examiner

GUIDEWIRE WITH DEFLECTABLE TIP

This patent application claims the benefit of provisional patent application Ser. No. 60/366,739 filed on Mar. 22, 2002.

BACKGROUND OF THE INVENTION

1. Field of the Invention

The present invention relates to a steerable guidewire, and more particularly to a bi-directional steerable guidewire having a tip which may be very precisely "steered," or deflected. The guidewire is particularly suitable for use in conjunction with the insertion of a catheter into a vessel of the body, or alternatively, the guidewire may be used by itself to open obstructions within a vessel or to carry a therapeutic device for removing obstructions within a vessel.

2. Description of the Prior Art

For many years guidewires have included a core wire with the distal end being tapered and with a coil spring mounted on the tapered distal end. These guidewires have been used to facilitate the insertion of a catheter into a vessel of the body. Generally, the guidewire is inserted into a vessel, a catheter is inserted over the guidewire and the catheter is then moved through the vessel until the distal end of the catheter is positioned at a desired location. The guidewire is then retracted from the catheter and the catheter is left in the vessel. Alternatively, the guidewire may be first inserted into the catheter with the distal portion of the guidewire extending beyond the distal end of the catheter. This assembly is then inserted into a vessel with the distal tip of the guidewire being used to facilitate movement of the guidewire and catheter through the vessel. Again, when the distal tip of the catheter has been placed in a desired location, the guidewire may be retracted thereby leaving the catheter in place within the vessel.

Another common application for guidewires is that of using the distal tip of the guidewire for removing an obstruction within a vessel. Often times this procedure is accomplished by inserting the guidewire within a vessel, moving the distal tip of the guidewire into contact with the obstruction and then very gently tapping the distal tip of the guidewire against the obstruction until the guidewire passes through the obstruction. Alternatively, various types of devices may be placed on the distal end of a guidewire for actively opening an obstruction within the vessel. Examples of such devices which may be placed on the end of the guidewires are disclosed in the following Robert C. Stevens: U.S. Pat. Nos. 5,116,350; 5,078,722; 4,936,845; 4,923,462; and, 4,854,325.

While most guidewires used today do not include a mechanism for deflecting or steering the tip of the guidewire, it is very desirable to provide tip steering in order to facilitate movement of the guidewire through the tortuous vessels of the body. There are many patents directed toward different mechanisms for deflecting the distal tip of a guidewire in order to steer the guidewire. Examples of such guidewires are disclosed in the following patents: U.S. Pat. No. 4,815,478 to Maurice Buchbinder, et al., U.S. Pat. No. 4,813,434 to Maurice Buchbinder, et al., U.S. Pat. No. 5,037,391 to Julius G. Hammerslag, et al., U.S. Pat. No. 5,203,772 to Gary R. Hammerslag, et al., U.S. Pat. No. 6,146,338 to Kenneth C. Gardeski, et al., U.S. Pat. No. 6,126,649 to Robert A. VanTassel, et al., U.S. Pat. No. 6,059,739 to James C. Baumann and U.S. Pat. No. 5,372,587 to Julius G. Hammerslag, et al. U.S. Pat. No. 4,940,062 to Hilary J. Hampton, et al., discloses a balloon catheter having a steerable tip section. All of the above-identified patents are incorporated herein by reference.

While each of the latter group of patents disclose guidewires having some degree of steerability, there is a need to have a guidewire with very precise steering in a guidewire of a very small diameter which is suitable for the purposes described above. More particularly, there is an important need for a very small diameter guidewire having a distal tip which may be deflected very precisely in either of two directions to enhance steerability and which is suitable for vascular applications.

SUMMARY OF THE INVENTION

In accordance with one aspect of the present invention, there is provided a very small diameter steerable guidewire having a deflectable tip which includes an elongated flexible tubing, a flexible helical coil attached to the distal portion of the flexible tubing, an elongated deflection member which is slidably disposed within the tubing and within the helical coil. The proximal portion of the deflection member is of a cylindrical configuration and the distal portion is tapered to form a deflection ribbon. Alternatively, the deflection member may take the form of a proximal cylindrical wire which is attached at its distal end to a deflection ribbon. In addition, a retaining ribbon is attached to the distal end of the flexible tubing and is oriented to extend in a plane which is generally parallel to the plane of the ribbon portion of the deflection member. An attachment member which may take the form of a rounded bead, preferably formed from epoxy, is bonded to the distal end of the helical coil, the distal end of the deflection ribbon and the distal end of the retaining ribbon so that longitudinal movement of the deflection member causes the distal end of the helical coil to be deflected.

In accordance with another aspect of the present invention, the retaining ribbon and the deflection ribbon are preferably pre-shaped into a curved configuration to thereby cause the flexible helical coil to be biased into a normally curved shape.

In accordance with a further aspect of the present invention, the distal portion of the deflection ribbon engages the attachment member, or rounded bead, at a location offset from the center of the attachment member, and the distal portion of the retaining ribbon engages the attachment member at a location offset from the center of the attachment member. Preferably, the retaining ribbon engages the attachment member at a location offset from the center portion of the attachment member in the opposite direction from the offset location of the deflection ribbon.

In accordance with still another aspect of the present invention, the deflection ribbon and the retaining ribbon are connected to each other within the attachment member. Preferably these two elements are formed as a single unitary element. In a preferred embodiment of the invention the cylindrical deflection member is flattened to form the deflection ribbon and is further flattened at its distal end to form the retaining ribbon. The retaining ribbon is bent 180 degrees with respect to the deflection ribbon to form a generally U-shaped bend to thereby establish a predetermined spacing between the ribbons and to also cause these ribbons to remain parallel to each other.

DESCRIPTION OF THE PREFERRED EMBODIMENT

Figure 1:
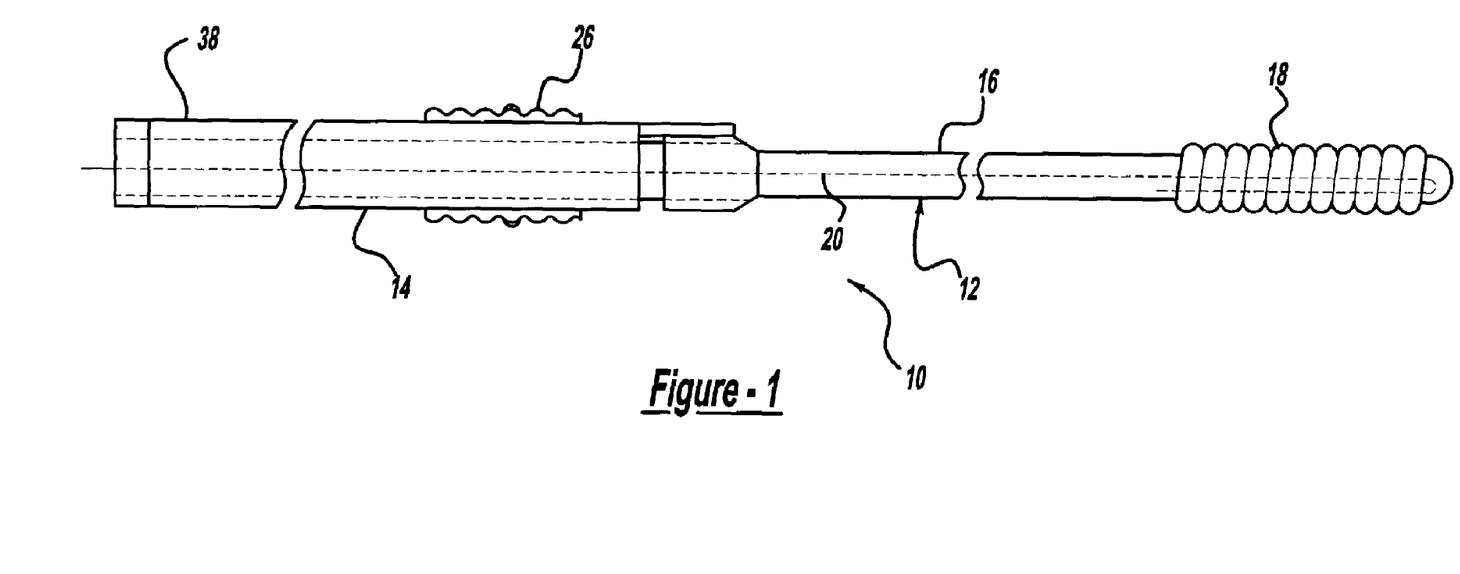
FIG. 1 is an enlarged elevational view of the steerable guidewire with a deflectable tip and control handle in accordance with the one aspect of the present invention.

FIG. 1 generally illustrates a steerable guidewire system 10 which embodies the present invention and comprises a steerable guidewire 12 coupled to a control handle 14. More particularly, the steerable guidewire comprises an elongated hypotube 16, a helical coil 18 attached to and extending from the distal end of the hypotube 16. The helical coil 18 is preferably formed from platinum tungsten with the proximal turns being wound such that adjacent turns of the proximal portion are in contact with each other.

While the preferred embodiment of the present invention includes the helical coil 18, this element may take the form of any flexible cylindrical member, such as for example a thin metallic tube with or without portions of the tube removed by, for example laser cutting, so as to form a very flexible cylindrical member. An elongated, deflection member 20 extends from the proximal end of the control handle through the hypotube 16 and through the helical coil 18, and is connected into an attachment member, or rounded bead 22, which is disposed at the distal tip of the helical coil 18. In addition, a retaining ribbon 24 is connected to the distal end of the hypotube 16 and is also connected to the rounded bead 22.

The control handle 14 generally comprises a slidable control knob 26 which may be moved longitudinally with respect to the control handle. The control handle 14 is coupled to the deflection member 20. As will be discussed in more detail, the longitudinal movement of the slidable control knob 26 causes deflection of the distal tip of the guidewire in either an upward or downward direction.

Figure 2:
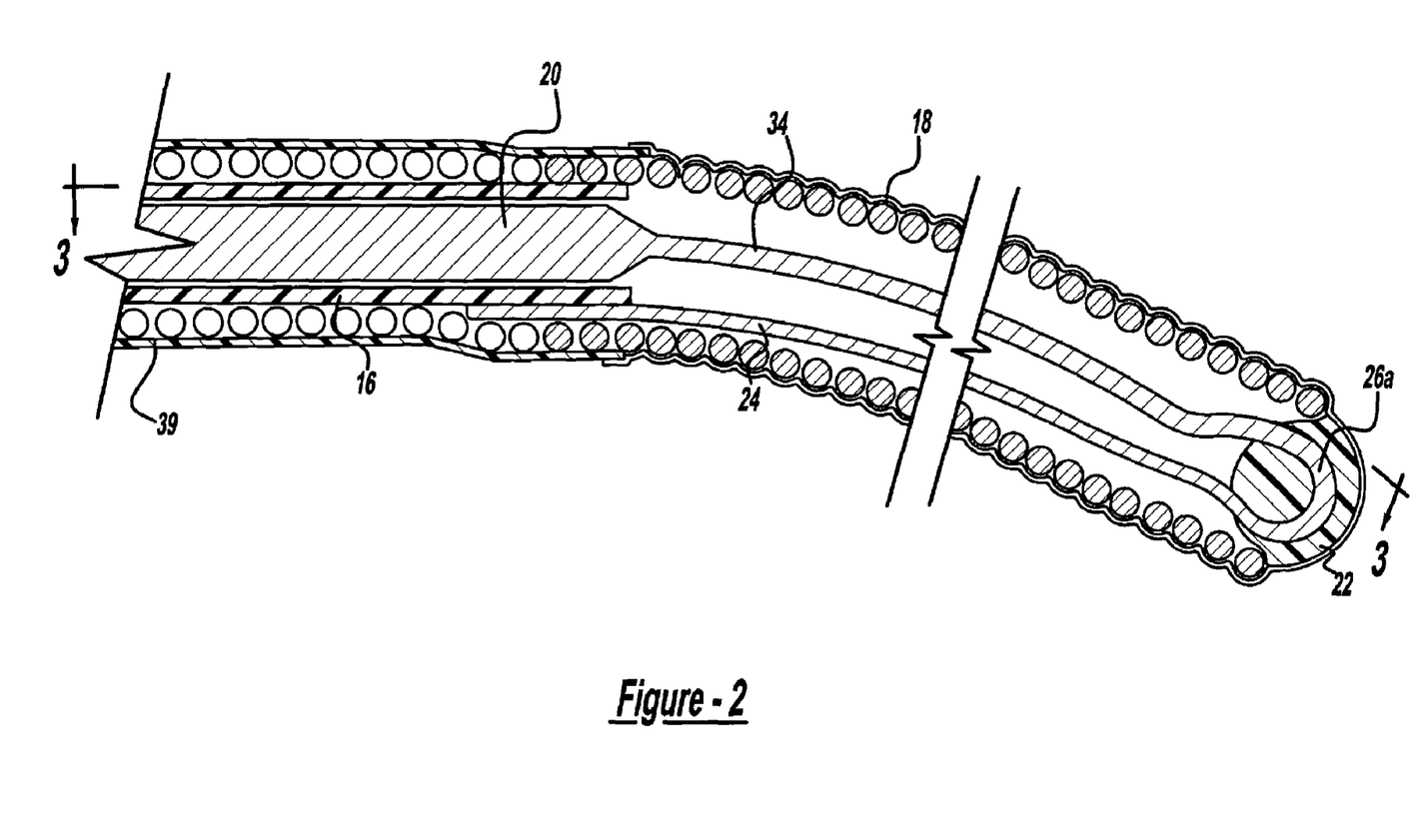
FIG. 2 is an enlarged sectional view showing the distal end of the steerable guidewire in its normal pre-shaped position.
Figure 3:
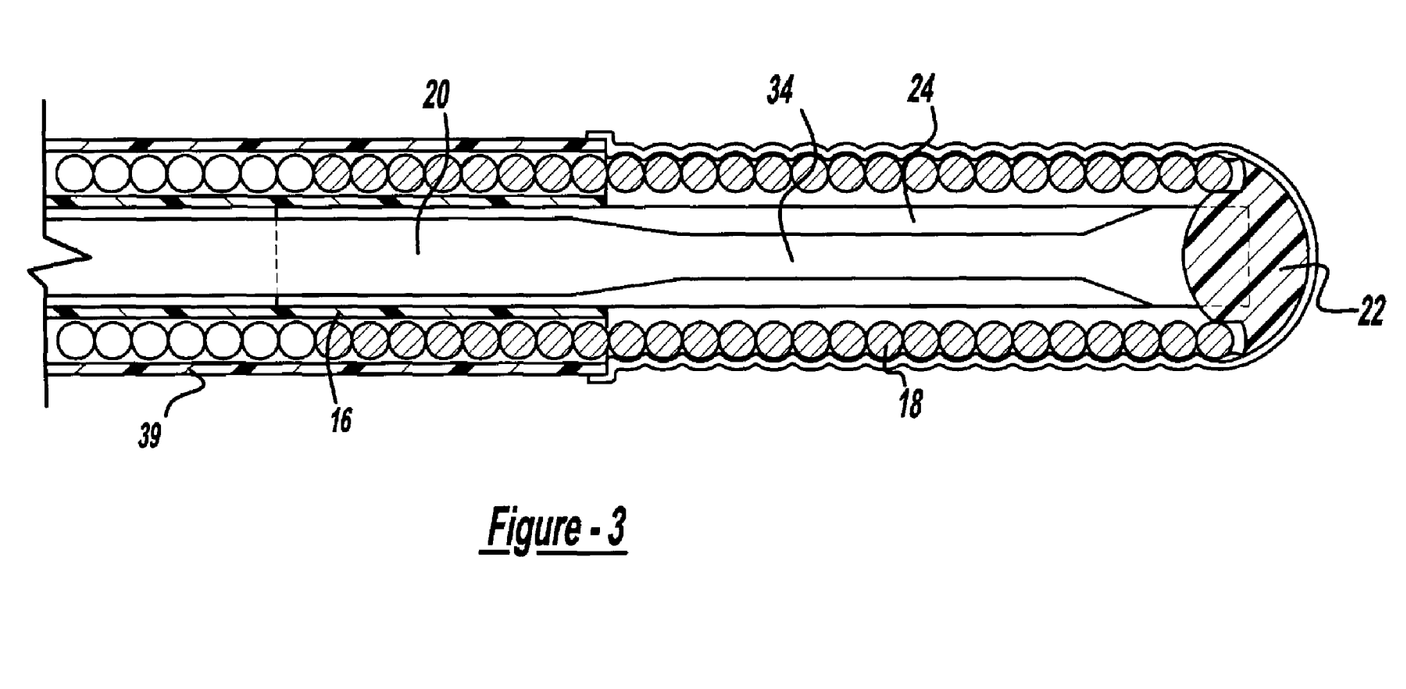
FIG. 3 is an enlarged sectional view showing the distal end of the steerable guidewire of FIG. 2 taken along the line 3—3.

FIGS. 2 and 3 illustrate in more detail the distal portion of the steerable guidewire 12. As may be appreciated, FIG. 3 is a view of the guidewire 12 shown in FIG. 2 with the guidewire being rotated 90 degrees about its longitudinal axis. More particularly, the proximal end of the helical coil 18 is bonded, preferably by use of an epoxy, to the outer surface near the distal end of the hypotube 16. The elongated deflection member 20 takes the form of a small diameter cylindrical deflection member 20 having an intermediate portion which is flattened to form a thin deflection ribbon 34 having a thickness of approximately 0.002 inches. The distal end of the cylindrical deflection member 20 is further flattened to a thickness of approximately 0.0015 inches and is bent back 180 degrees to form a U-shaped bend 26a between the deflection ribbon 34 and the retaining ribbon 24. The proximal end of the retaining ribbon 24 is bonded, preferably by use of epoxy, to the outer surface of the distal end of the hypotube 16. The retaining ribbon 24 is aligned in a plane parallel to the plane of the deflection ribbon 34 and the U-shaped portion between the ribbons is encapsulated by the attachment member which preferably takes the form of a rounded epoxy bead 22 bonded to the distal tip of the helical coil 18.

As may be appreciated, with this unitary construction of the ribbon members, these members remain aligned so that both lie in planes parallel to each other. In addition, the U-shaped bend portion when encapsulated into the rounded bead 22 causes the retaining ribbon and deflection ribbon to be properly spaced with respect to each other.

As illustrated in FIG. 2, the retaining ribbon 24 is preferably attached to the rounded bead 22 at a position offset from the center of the bead in the same direction that the retaining ribbon 24 is offset from the longitudinal axis of the steerable guidewire 12. In addition, the deflection ribbon 34 is attached to the bead at a position offset from the center of the bead in an opposite direction from the offset of the retaining ribbon 24.

Also, as may be seen in FIG. 2, the deflection ribbon 34 and the retaining ribbon 24 are pre-shaped into an arcuate, or curved, configuration to thereby maintain the helical coil 18 in a normally curved configuration. The ribbons 24, 34 are pre-shaped such that the distal tip of the guidewire curves away from the longitudinal axis of the guidewire in a direction toward that side of the guidewire containing the retaining ribbon 24.

Figure 4:
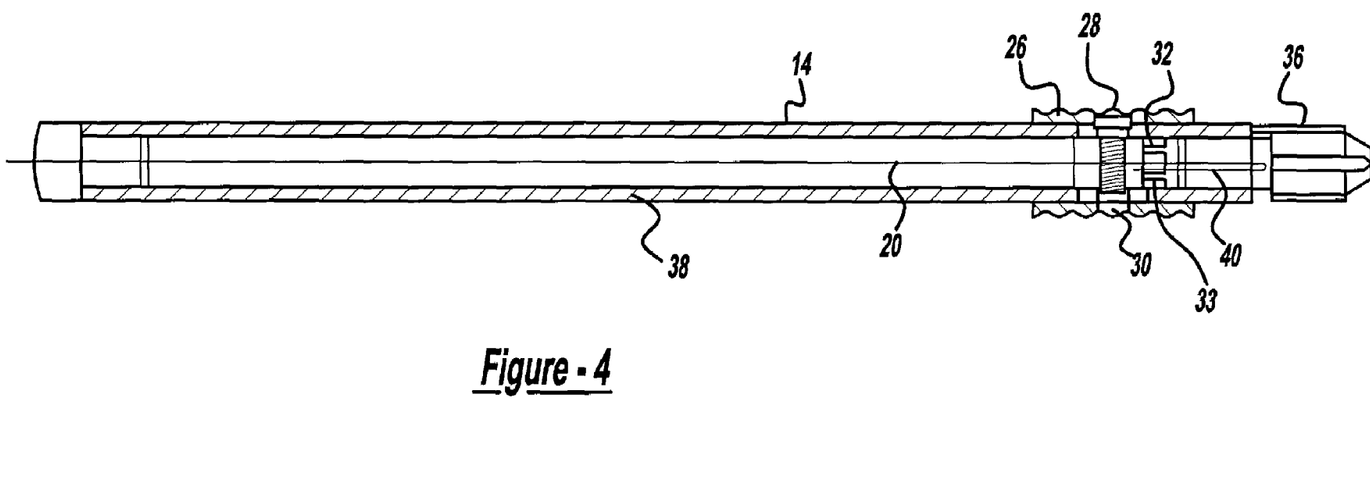
FIG. 4 is a partially sectional view showing the control handle for the steerable guidewire; and, FIGS. 5 and 5A are sectional views showing the steerable guidewire deflected from its normal position to opposite extremes of deflection.

FIG. 4 illustrates in more detail the control handle 14 which includes a cylindrical body portion 38 with the slidable control knob 26 being mounted for longitudinal movement along the cylindrical body portion 38 of the control handle 14. The pair of set screws 28, 30 extend through the slidable control knob 26 and lock onto the elongated deflection member 20 which extends through the control handle 14. In addition, the control handle 14 includes a coaxial hypotube 40 which is disposed about the deflection member 20 and which is locked in place within the control handle by another set of set screws 32, 33. The coaxial hypotube 40 serves to prevent the deflection member 20 from buckling as the slidable control knob is moved in a distal direction. Still further, the control handle 14 includes a pin vise 36 which serves to clamp onto the deflection member 20.

Figure 5:
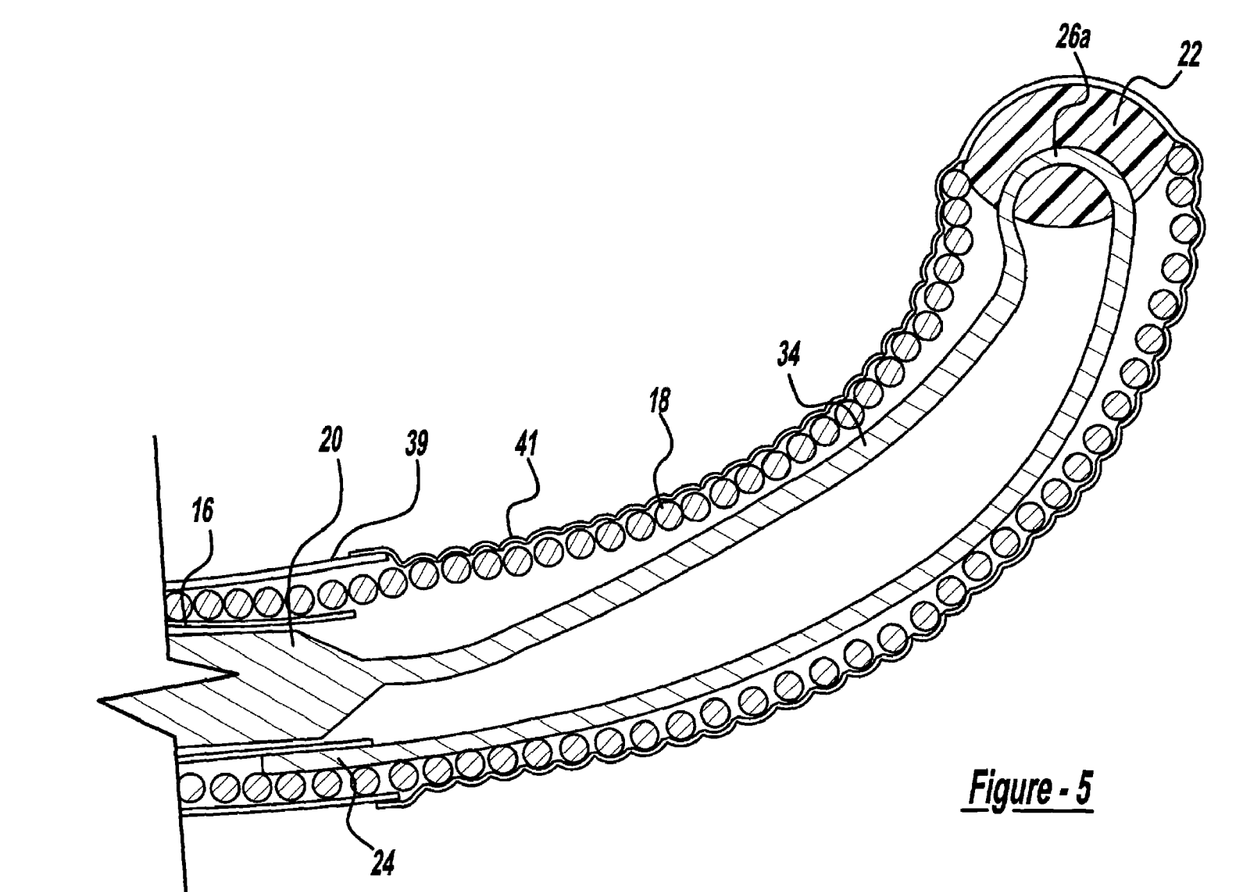
Figure 5A:
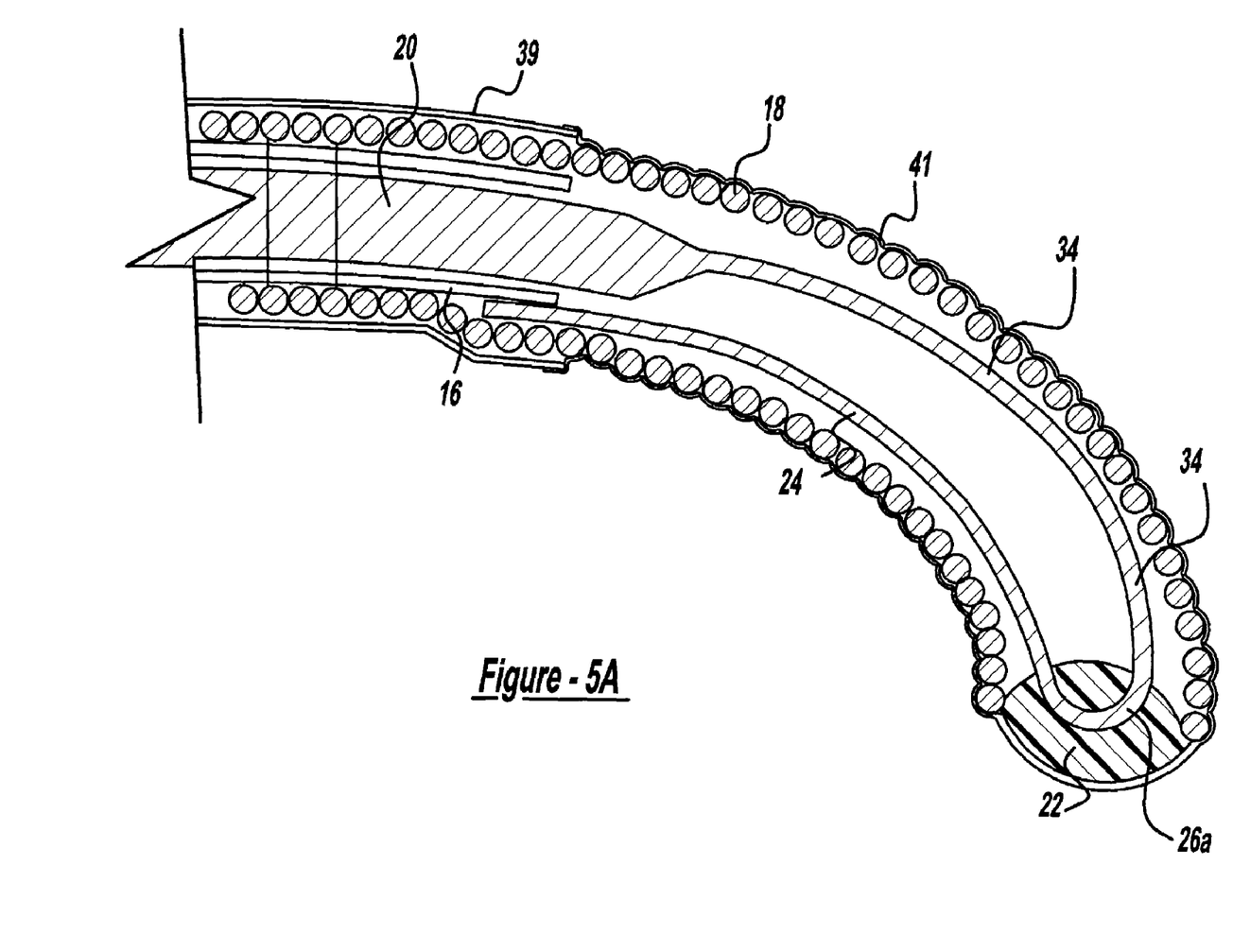

In operation, as previously described, the distal tip of the steerable guidewire 12 is normally biased into a downwardly curved position as illustrated in FIG. 2 because of the curve of the pre-shaped deflection ribbon 34 and the retaining ribbon 24. When the slidable control knob 26 is moved distally, the deflection member 20 will be moved distally thereby causing the deflection ribbon 34 to move in a distal direction. As the deflection ribbon is moved distally, a force is applied to the top portion of the rounded bead 22. The retaining ribbon 24 is attached to the lower portion of the bead 22 to thereby maintain the bead at a fixed distance from the distal end of the hypotube 16. As the deflection ribbon 34 is moved to the right, the tip of the guidewire is caused to deflect downwardly to a maximum position of deflection as shown in FIG. 5A. Since the deflection ribbon 34 and the retaining ribbon 24 are pre-shaped prior to any activation of the steerable guidewire, the amount of force required to deflect the guidewire in this direction is very small thereby preventing buckling of the deflection ribbon 34 as the deflection ribbon is pushed distally. As the deflection ribbon 34 is moved distally, the upper turns of the helical coil become slightly stretched and the lower turns of the coil become slightly compressed. The deflection member 20 has a diameter of about 0.0065 inches and the deflection ribbon has a thickness of about 0.002 inches to thereby provide sufficient stiffness to prevent the buckling of these elements when the deflection member 20 is pushed distally. This construction also provides sufficient stiffness to transmit the necessary force to the distal tip of the guidewire.

When the slidable control knob 26 is moved in a proximal direction (to the left in FIG. 4) the deflection member 20 will be pulled to the left to thereby cause the deflection ribbon 34 to pull on the top portion of the bead 22. Since again the retaining ribbon 24 causes the lower portion of the bead to remain at a fixed distance from the distal end of the hypotube 16, the tip of the guidewire 12 is caused to bend in an upward direction to a maximum deflection as shown in FIG. 5. Since the deflection ribbon 34 is in tension when the deflection member 20 is pulled, there is no concern for buckling of the deflection ribbon 34. As the deflection ribbon 34 is moved proximally as shown in FIG. 5, the upper coil turns become slightly compressed and the lower coil turns become somewhat stretched.

In a preferred embodiment of the present invention, the elongated deflection member 20, retaining ribbon 24 and deflection ribbon 34 are constructed of nitinol, but these elements may be formed from other flexible materials including polymers. The helical coil 18 preferably has an outside coil diameter of about 0.013 inches and is constructed from an alloy comprised of about 92 percent platinum and 8 percent tungsten, but this element may also be constructed from numerous other materials. It is desirable that the coil exhibit the characteristic of being radiopaque to X-rays to assist in the positioning of the distal tip of the steerable guidewire 12. The deflection member 20 is formed from a single cylindrical nitinol wire of about 0.0065 inches in diameter having an intermediate portion which is flattened to form the deflection ribbon 34 with a thickness of about 0.002 inches, and a distal portion which is flattened to form the retaining ribbon 24 with a thickness of about 0.0015 inches. The retaining ribbon 24 is bent back 180 degrees to form a generally U-shaped bend, which is subsequently encapsulated within the rounded bead 22. The rounded bead 22 is preferably formed with epoxy, but may be formed with soldering or by welding.

It has been found that the addition of graphite between the deflection member 20 and deflection ribbon 34, and the inner lumen of the hypotube 16 provides lubrication. Other lubricants, such as Teflon or MDX may be used for this purpose. The helical coil 18 is preferably coated with an elastomeric polymer 41 on its distal end to act as a sealant preventing the entry of blood and contrast media into the guidewire and a fluorinated polymer 39, such as Teflon, on its proximal end for lubrication purposes.

It may be seen that the guidewire as disclosed may be very easily and very precisely deflected in either of two directions for very precise steering of the guidewire through the vessels of the body. As may be apparent, the disclosed guidewire may be used for placement of a catheter within the vasculature of the human body, it may be used by itself to cross an obstruction within the vessels or it may be used to carry a therapeutic device mounted on the distal end of the guidewire for purposes of removing obstructions which may exist within a vessel of the body.

The preceding specific embodiment is illustrated of the practice of this invention. It is to be understood, however, that other variations may also be employed without departing from the spirit and scope of the invention as hereinafter claimed.

That which is claimed is:

1. A bi-directional steerable guidewire having a deflectable tip which comprises:
    an elongated flexible tubing having proximal and distal portions;
    a flexible helical coil having proximal and distal ends, the proximal end of said helical coil is attached to the distal portion of the flexible tubing;
    an elongated deflection member having proximal and distal portions and being slidably disposed within said tubing and within said helical coil, the distal portion of said deflection member being flattened to form a deflection ribbon which extends in a plane;
    a retaining ribbon having proximal and distal ends, the proximal end of the retaining ribbon is attached to the distal portion of the flexible tubing and the retaining ribbon is oriented to extend in a plane which is generally parallel to the plane of the deflection ribbon; and,
    an attachment member engaging the distal end of the helical coil, the distal portion of the deflection member and the distal end of the retaining ribbon so that longitudinal movement of the deflection member in a distal direction causes the distal end of the helical coil to be deflected in one direction and longitudinal movement of the deflection member in a proximal direction causes the distal end of the helical coil to deflect in another opposite direction, said attachment member takes the form of a rounded bead which contacts the distal end of the helical coil to define a circular surface at the distal end of the coil and the deflection ribbon engages the rounded bead at a location offset from the center of the circular surface of the rounded bead, said distal end of the retaining ribbon engages the rounded bead at a location offset from the center of the circular surface in an opposite direction from the offset location of the deflection ribbon.

2. A steerable guidewire as defined in claim 1, wherein the deflection member and the retaining ribbon are joined to each other within the rounded bead.

3. A steerable guidewire as defined in claim 2, wherein the deflection ribbon and the retaining ribbon are formed as a single unitary element.

4. A steerable guidewire as defined in claim 3, wherein the deflection ribbon and the retaining ribbon are joined to form a generally U-shaped configuration to thereby provide a predetermined spacing between the deflection ribbon and the retaining ribbon and to maintain the deflection ribbon and the retaining ribbon in planes which are parallel to each other.

5. A steerable guidewire as defined in claim 4, wherein the deflection ribbon is formed by flattening an intermediate portion of the deflection member and the retaining ribbon is formed by flattening a distal portion of the deflection member.

6. A steerable guidewire as defined in claim 5, wherein the retaining ribbon is of a thickness which is less than the thickness of the deflection ribbon.

7. A steerable guidewire as defined in claim 6, wherein the deflection ribbon is of a thickness equal to about 0.002 inches and the retaining ribbon is of a thickness equal to about 0.0015 inches.

8. A bi-directional steerable guidewire having a deflectable tip which comprises:
    an elongated flexible tubing having proximal and distal portions;
    a flexible helical coil having proximal and distal ends, the proximal end of said helical coil is attached to the distal portion of the flexible tubing;
    an elongated deflection member having proximal and distal portions and being slidably disposed within said tubing and within said helical coil, the distal portion of said deflection member being tapered;

an elongated retaining member having proximal and distal ends, the proximal end of the retaining member is attached to the distal portion of the flexible tubing, said retaining member is pre-shaped in an arcuate configuration to thereby cause the flexible helical coil to be normally biased into a curved shape; and, an attachment member engaging the distal end of the helical coil, the deflection member and the distal end of the retaining member so that longitudinal movement of the deflection member in a distal direction causes the distal end of the helical coil to be deflected in one direction and longitudinal movement of the deflection member in a proximal direction causes the distal end of the helical coil to deflect in an opposite direction, wherein a portion of the attachment member extends across the distal end of the helical coil and the distal portion of the deflection member engages the attachment member at a location offset from the center of the portion of the attachment member extending across the distal end of the helical coil.

9. A steerable guidewire as defined in claim 8, wherein the distal end of the retaining member engages the attachment member at a location offset from the center of the portion of the attachment member extending across the distal end of the helical coil.

10. A steerable guidewire as defined in claim 9, wherein the distal end of the retaining member engages the attachment member at a location offset from the center portion of the attachment member in an opposite direction from the offset location of the deflection member.

11. A steerable guidewire as defined in claim 10, wherein the deflection member and the retaining member are joined to each other within the attachment member.

12. A steerable guidewire as defined in claim 11, wherein the deflection member and the retaining member are formed as a single unitary element.

13. A steerable guidewire as defined in claim 12, wherein the junction between the deflection member and the retaining member form a generally U-shaped configuration to thereby provide a predetermined spacing between the distal portion of the deflection member and the distal end of the retaining member.

14. A steerable guidewire as defined in claim 13, wherein the attachment member takes the form of a rounded bead.

15. A steerable guidewire having a deflectable tip which comprises:
an elongated flexible tubing having proximal and distal portions;
a flexible helical coil having proximal and distal ends, the proximal end of said helical coil is attached to the distal portion of the flexible tubing;
an elongated deflection member comprised of proximal and distal portions and being slidably disposed within said tubing and within said helical coil, the proximal portion of the deflection member being of a cylindrical cross section and the distal portion of said deflection member takes the form a deflection ribbon which extends in a plane, said distal portion of the deflection member and the deflection ribbon are formed from a wire of a circular cross section and in which the distal portion of the deflection member is flattened to form the deflection ribbon;
a retaining ribbon having proximal and distal ends, the proximal end of the retaining ribbon is attached to the distal portion of the flexible tubing and the retaining ribbon is oriented to extend in a plane which is generally parallel to the plane of the deflection ribbon; and, an attachment member engaging the distal end of the helical coil, the distal portion of the deflection member and the distal end of the retaining ribbon so that longitudinal movement of the deflection member in a distal direction causes the distal end of the helical coil to be deflected in one direction and longitudinal movement of the deflection member in a proximal direction causes the distal end of the helical coil to deflect in another opposite direction, said attachment member takes the form of a rounded bead which contacts the distal end of the helical coil to define a circular surface at the distal end of the coil and the deflection ribbon engages the rounded bead at a location offset from the center of the circular surface of the rounded bead.

16. A steerable guidewire as defined in claim 15, wherein the distal end of the retaining ribbon engages the rounded bead at a location offset from the center of the circular surface of the rounded bead.

17. A steerable guidewire as defined in claim 16, wherein the distal end of the retaining ribbon engages the rounded bead at a location offset from the center of the circular surface in an opposite direction from the offset location of the deflection ribbon.

18. A steerable guidewire as defined in claim 17, wherein the deflection member and the retaining ribbon are joined to each other within the rounded bead.

19. A steerable guidewire as defined in claim 18, wherein the deflection ribbon and the retaining ribbon are joined to form a generally U-shaped configuration to thereby provide a predetermined spacing between the deflection ribbon and the retaining ribbon and to maintain the deflection ribbon and the retaining ribbon in planes which are parallel to each other.

20. A steerable guidewire as defined in claim 19, wherein the deflection ribbon is formed by flattening an intermediate portion of the deflection member and the retaining ribbon is formed by flattening the distal portion of the deflection member.

21. A steerable guidewire as defined in claim 20, wherein the retaining ribbon is of a thickness which is less than the thickness of the deflection ribbon.

22. A steerable guidewire as defined in claim 21, wherein the proximal portion of the elongated flexible tubing is coupled to a control handle and the elongated deflection member is mounted with the control handle for longitudinal movement, said control handle includes a movable knob which is coupled to the elongated deflection member for longitudinal positioning of the deflection member, and said control handle is coupled to the elongated flexible tubing with a release mechanism so that the handle may be removed from the guidewire.

23. A steerable guidewire as defined in claim 22, wherein the elongated deflection member extends through the entire length of the control handle and beyond the proximal end of the control handle.

24. A bi-directional steerable guidewire having a deflectable tip which comprises:
an elongated flexible tubing having proximal and distal portions;
a flexible cylindrical member having proximal and distal ends, the proximal end of said cylindrical member is attached to the distal portion of the flexible tubing;
an elongated deflection member having proximal and distal portions and being slidably disposed within said tubing and within said cylindrical member, the distal portion of said deflection member being tapered, said distal portion of the elongated deflection member takes the form of a thin ribbon which extends in a plane;

an elongated retaining member having proximal and distal ends, the proximal end of the retaining member is attached to the distal portion of the flexible tubing, said retaining member is pre-shaped in an arcuate configuration to thereby cause the flexible cylindrical member to be normally biased into a curved shape; and said retaining member takes the form of a thin ribbon which is oriented to extend in a plane which is generally parallel to the plane of the deflection member; and, an attachment member engaging the distal end of the cylindrical member, the deflection member and the distal end of the retaining member so that longitudinal movement of the deflection member in a distal direction causes the distal end of the cylindrical member to be deflected in one direction and longitudinal movement of the deflection member in a proximal direction causes the distal end of the cylindrical member to deflect in an opposite direction, said attachment member takes the form of a rounded bead and wherein a portion of the attachment member extends across the distal end of the cylindrical member, the distal portion of the deflection member engages the attachment member at a location offset from the center of the portion of the attachment member extending across the distal end of the cylindrical member.

25. A steerable guidewire as defined in claim 24, wherein the distal end of the retaining member engages the attachment member at a location offset from the center of the portion of the attachment member extending across the distal end of the cylindrical member.

26. A steerable guidewire as defined in claim 25, wherein the distal end of the retaining member engages the attachment member at a location offset from the center portion of the attachment member in an opposite direction from the offset location of the deflection member.

27. A steerable guidewire as defined in claim 26, wherein the deflection member and the retaining member are joined to each other within the attachment member.

28. A steerable guidewire as defined in claim 27, wherein the deflection member and the retaining member are formed as a single unitary element.

29. A steerable guidewire as defined in claim 28, wherein the junction between the deflection member and the retaining member form a generally U-shaped configuration to thereby provide a predetermined spacing between the distal portion of the deflection member and the distal end of the retaining member.

* * * * *